(12) United States Patent
Hancock

(10) Patent No.: US 6,331,157 B2
(45) Date of Patent: *Dec. 18, 2001

(54) APPARATUS AND METHODS FOR OFF-PUMP CARDIAC SURGERY

(75) Inventor: Andrew H. Hancock, Fremont, CA (US)

(73) Assignee: Heartport, Inc., Redwood City, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,630

(22) Filed: Apr. 15, 1999

(51) Int. Cl.[7] ................................... A16B 17/02
(52) U.S. Cl. .......................................... 600/232
(58) Field of Search ......................... 600/201, 210, 600/228, 231, 232, 233

(56) References Cited

U.S. PATENT DOCUMENTS

| | | |
|---|---|---|
| Re. 34,150 | 12/1992 | Santili et al. . |
| 2,693,795 * | 11/1954 | Grieshaber ............................ 600/232 |
| 2,850,008 * | 9/1958 | Resch ..................................... 600/232 |
| 3,384,078 | 5/1968 | Gauthier . |
| 3,572,326 | 3/1971 | Jensen . |
| 3,710,783 | 1/1973 | Jascalevich . |
| 3,724,449 | 4/1973 | Gauthier . |
| 3,782,370 | 1/1974 | McDonald . |
| 3,807,393 | 4/1974 | McDonald . |
| 3,863,639 | 2/1975 | Kleaveland . |
| 4,151,838 | 5/1979 | Crew . |
| 4,274,398 * | 6/1981 | Scott, Jr. ............................... 600/233 |
| 4,344,420 | 8/1982 | Forder . |
| 4,355,631 | 10/1982 | LeVahn . |
| 4,457,300 | 7/1984 | Budde . |
| 4,492,229 * | 1/1985 | Grunwald ............................ 600/232 |
| 4,622,955 | 11/1986 | Fakhrai . |
| 4,627,421 | 12/1986 | Symbas et al. . |
| 4,702,230 | 10/1987 | Pelta . |
| 4,726,356 | 2/1988 | Santilli et al. . |
| 4,747,395 | 5/1988 | Brief . |
| 4,813,401 | 3/1989 | Grieshaber . |

(List continued on next page.)

FOREIGN PATENT DOCUMENTS

| | | |
|---|---|---|
| 3834358 | 12/1990 | (DE) . |
| 4028651 | 3/1992 | (DE) . |
| 0769269 | 4/1997 | (EP) . |
| 0792620 | 9/1997 | (EP) . |
| 473451 * | 1/1915 | (FR) ..................................... 600/232 |
| 2267827 | 12/1993 | (GB) . |

OTHER PUBLICATIONS

Ancalmo and Ochsner, "A Modified Sternal Retractor," *Ann Thorac Surg*, 1976;21(2):174.

Beg et al., "Internal Mammary Retractor," *Ann Thorac Surg*, 1985;39(3):286–287.

(List continued on next page.)

*Primary Examiner*—Paul J. Hirsch
(74) *Attorney, Agent, or Firm*—Hoekendijk & Lynch, LLP.

(57) ABSTRACT

The invention provides an apparatus for performing surgery on a heart of a patient comprising a first arm, a second arm and an actuator, the actuator moving the first arm relative to the second arm. The apparatus further includes a first blade on the first arm and a second blade on the second arm, the first and second blades having first and second surfaces facing away from each other, the first and second surfaces being adapted to atraumatically engage tissue or bone for the retraction thereof. The apparatus also includes a stabilizer adapted to be mounted to one of the first and second arms and having a foot, the foot being configured to atraumatically engage the surface of the heart. In a various embodiments, the apparatus includes removable blades mounted to the arms, suture stays removably mounted to the arms, and multiple rails for mounting the stabilizer in various positions.

4 Claims, 16 Drawing Sheets

U.S. PATENT DOCUMENTS

| | | |
|---|---|---|
| 4,829,985 | 5/1989 | Couetil . |
| 4,852,552 * | 8/1989 | Chava .................................. 600/232 |
| 4,865,019 | 9/1989 | Phillips . |
| 4,884,559 | 12/1989 | Collins . |
| 4,949,707 | 8/1990 | LeVahn et al. . |
| 4,989,587 | 2/1991 | Farley . |
| 5,027,793 | 7/1991 | Engelhardt et al. . |
| 5,052,373 * | 10/1991 | Michelson ............................ 600/232 |
| 5,074,858 | 12/1991 | Martinez . |
| 5,088,472 | 2/1992 | Fakhrai . |
| 5,125,396 | 6/1992 | Ray . |
| 5,167,223 | 12/1992 | Koros et al. . |
| 5,365,921 * | 11/1994 | Bookwatter et al. ................. 600/232 |
| 5,730,757 | 3/1998 | Benetti et al. . |
| 5,772,583 * | 6/1998 | Wright et al. ......................... 600/232 |
| 5,795,291 * | 8/1998 | Keros et al. .......................... 600/232 |
| 5,894,843 | 4/1999 | Benetti et al. . |
| 5,944,736 | 8/1999 | Taylor et al. . |
| 5,967,972 * | 10/1999 | Santilli et al. ........................ 600/229 |
| 5,976,080 * | 11/1999 | Farascioni ............................. 600/201 |
| 5,984,867 * | 11/1999 | Deckman et al. .................... 600/232 |
| 6,036,641 * | 3/2000 | Taylor et al. ......................... 600/232 |
| 6,102,854 * | 8/2000 | Cartier et al. ........................ 600/232 |
| 6,190,311 | 2/2001 | Glines et al. . |
| 6,213,941 | 4/2001 | Benetti et al. . |

OTHER PUBLICATIONS

Chaux and Blanche, "A New Concept in Sternal Retraction: Applications for Internal Mammary Artery Dissection and Valve Replacement Surgery," *Ann Thorac Surg*, 1986;42:473–474.

McKeown et al., "A Modified Sternal Retractor for Exposure of the Internal Mammary Artery," *Ann Thorac Surg*, 1981;32(6): 619.

Sugarbaker et al., Section VI, Chapter 26, Surgical Procedures to Resect and Replace the Esophagus, pp. 885–910, no date.

* cited by examiner

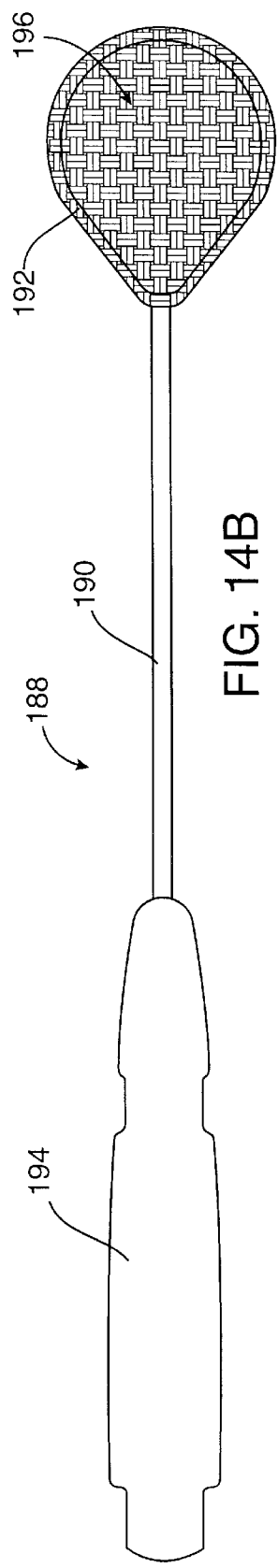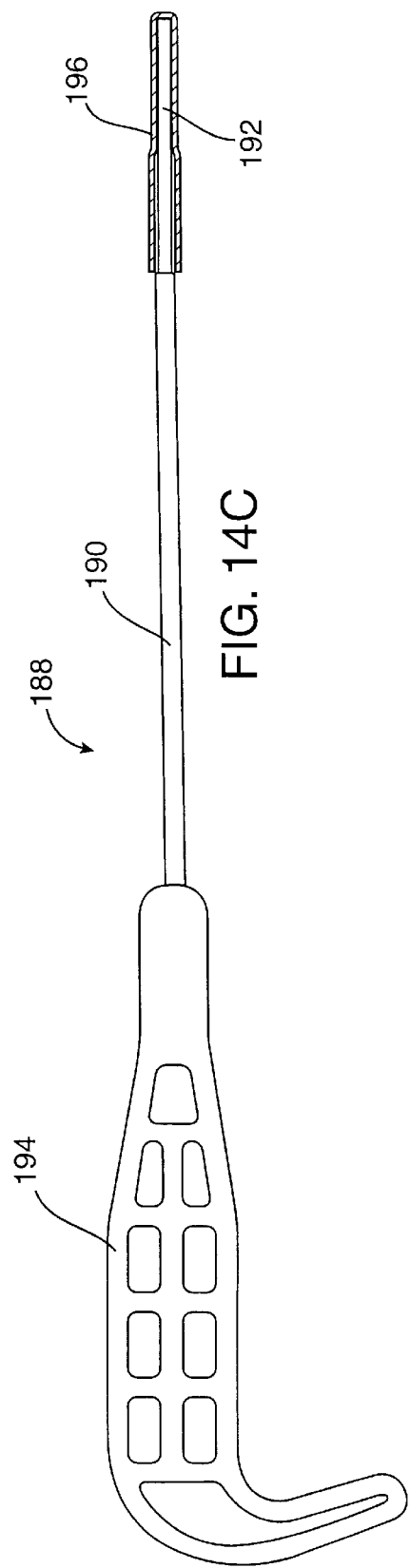

APPARATUS AND METHODS FOR OFF-PUMP CARDIAC SURGERY

FIELD OF THE INVENTION

The present invention relates generally to surgical instruments, and more specifically to retractors and instruments for performing heart surgery.

BACKGROUND OF THE INVENTION

In conventional heart surgery, an incision is made in the chest, either through the sternum (a median sternotomy) or between the ribs (a thoracotomy) in order to gain access into the chest cavity. A retractor is placed in the chest incision which allows the chest bones and tissue to be spread apart to create a wide opening. Surgical instruments are then placed through this opening to perform surgery on the heart.

One of the most common types of heart surgery is coronary artery bypass grafting, or CABG. In CABG, a blockage in one or more coronary arteries is bypassed by connecting a graft vessel to the coronary artery downstream of the blockage. The technique of connecting the graft vessel to the coronary artery is known as anastomosis. The graft vessel may be a mammary artery dissected from the chest wall, wherein the upstream end of the artery is left intact and the downstream end is attached to the coronary artery. Alternatively, the graft vessel may be a section of artery or vein from elsewhere in the patient's body, or an artificial vascular graft, wherein the upstream end of the graft is attached to an artery such as the aorta, and the downstream end is connected to the coronary artery. In this way, multiple coronary artery blockages at various locations on the front, side or back of the heart may be bypassed using multiple graft vessels.

Conventionally, CABG is performed with the heart stopped, while the patient is supported on cardiopulmonary bypass, whereby the patient's blood is circulated by means of an extracorporeal pump and oxygenation system. In certain cases, however, CABG may be performed with the heart beating in a technique known as "beating heart" or "off-pump" coronary artery bypass (OPCAB), allowing cardiopulmonary bypass to be avoided. In OPCAB, the surface of the heart near the anastomosis site on the coronary artery is stabilized using a specialized instrument while the heart continues to beat. This local stabilization keeps the anastomosis site as motionless as possible while the graft vessel is connected to the coronary artery. The coronary artery is temporarily occluded or a temporary shunt is inserted into the coronary artery during the anastomosis to keep the site free of blood.

The basic functions required in an OPCAB procedure include sternal or rib retraction, heart manipulation, heart stabilization, pericardial retraction, coronary traction and hemostasis. Sternal retraction involves prying apart the opposing halves of the divided sternum to open the chest cavity. Heart manipulation entails moving, turning or lifting the heart in order to access coronary arteries on the front, back or sides of the heart. Heart stabilization is the process of stabilizing the surface of the beating heart near the anastomosis site to allow the anastomosis to be performed. Pericardial retraction is used to pull the incised pericardium out of the way for better access to the heart. Coronary retraction involves placing a suture or silastic under the coronary arteries near the anastomosis site and exerting traction on the suture or silastic so as to better expose the coronary artery. This traction may also serve to occlude the coronary artery above and below the anastomosis site to provide hemostasis. In some cases, a temporary shunt may be inserted through an arteriotomy in the coronary artery to allow blood to flow past the anastomosis site during the procedure.

While surgeons have performed OPCAB surgery for a number of years using conventional instruments, in recent years, specially-designed instruments have been introduced to facilitate OPCAB. However, such instruments have suffered from certain drawbacks. For example, commercially available OPCAB systems frequently do not allow the surgeon a sufficient range of positions and degrees of freedom in positioning the stabilizing instrument and other devices utilized in the procedure. In addition, some commercially available OPCAB systems are disposable in major part or in their entirety, thus requiring the disposal of one system and the purchase of a new system each time a procedure is performed. On the other hand, entirely reusable systems frequently fail to provide the means to perform all of the required OPCAB functions described above, or are inferior in their performance of such functions.

What is needed therefore, is a system for performing OPCAB which facilitates sternal retraction, heart stabilization, pericardial retraction, coronary traction, and heart manipulation while the heart is beating. The system should provide maximum flexibility and degrees of freedom for positioning the heart stabilizing instrument and other components of the system. The system should have a minimum number of disposable components, and should be simple to use and cost-effective. The system should have the flexibility for use in either a sternotomy or a thoracotomy, and should be useful in both OPCAB surgery as well as other forms of cardiac surgery, with and without the heart beating.

SUMMARY OF THE INVENTION

The present invention provides systems for performing OPCAB and other types of cardiac surgery which overcome many of the drawbacks of current devices. The system provides additional degrees of freedom and ranges of position than currently available devices. The invention enables sternal or rib retraction, pericardial retraction, heart manipulation, coronary traction, and heart stabilization using a single integrated system. While providing such functionality, the systems of the invention preferably utilize an entirely reusable retraction platform, thereby eliminating the waste and cost associated with some current systems.

In a first embodiment, the invention provides an apparatus for performing surgery on a heart of a patient comprising a first arm, a second arm and an actuator, the actuator moving the first arm relative to the second arm. The apparatus further includes a first blade on the first arm and a second blade on the second arm, the first and second blades having first and second surfaces facing away from each other, the first and second surfaces being adapted to atraumatically engage tissue or bone for the retraction thereof. The apparatus also includes a stabilizer adapted to be mounted to one of the first and second arms and having a foot, the foot being configured to atraumatically engage the surface of the heart. In a preferred embodiment, the first and second blades are removably coupled to the first and second arms whereby the first and second blades may be removed and replaced with alternate blades. The ability to quickly and easily remove and replace blades allows the surgeon to select the ideal blade for the particular patient and procedure being performed. The apparatus of the invention thus allows blades of various size, shape, and material to be interchanged.

Preferably, the arms and blades are a biocompatible metal so as to be resterilizable and reusable, but alternatively either or both could be made of plastic or other suitable material and could be individually packaged and sterilized for single use.

In a second embodiment, the apparatus of the invention has a receptacle on at least one of the first and second arms. A suture stay is removably mounted to the receptacle, thus allowing sutures for pericardial retraction or for other purposes to be positioned in the suture stay and retained therein during a procedure. Preferably, the suture stay is plastic or other disposable material, allowing the suture stay to be removed from the receptacle and discarded after use. Usually, the suture stay will accomodate a plurality of individual sutures, and/or the arms include a plurality of receptacles to accomodate multiple suture stays. In an exemplary embodiment, the receptacle comprises a cavity in the arm adapted to receive the suture stay. A retention mechanism is provided on the suture stay and/or on the arm to releasably retain the suture stay in the cavity.

The suture stay preferably comprises a body having an inner edge and an outer edge and retention structure on the body for retaining the body on a blade of the surgical retractor. At least one channel extends through the body from the inner edge to the outer edge and is adapted to removably receive a suture therein. Additionally, a clamp is coupled to the body adjacent to the channel and is adapted to releasably retain the suture in the channel. Usually, the suture stay will be placed in a bag, pouch or other container and sterilized separately from the arms and other components of the apparatus.

In a further embodiment, an apparatus for performing surgery on a heart of a patient comprises a rack, a first arm and a second arm mounted to the rack, the first arm being movable relative to the rack and relative to the second arm. A first blade is mounted to the first arm and a second blade is mounted to the second arm, the first and second blades having first and second surfaces facing away from each other, the first and second surfaces being adapted to atraumatically engage tissue or bone for the retraction thereof. A first rail is disposed on the first arm, a second rail is disposed on the second arm, and a third rail is disposed on the rack. The apparatus further includes a stabilizer adapted to be coupled to any one of the first rail, second rail or third rail, the stabilizer having a foot, the foot being configured to atraumatically engage the surface of the heart.

The invention further provides a stabilizing device for stabilizing a site on an outer surface of a patient's heart to facilitate surgery thereon. In one embodiment, the stabilizing device comprises a shaft, a foot coupled to the shaft having a contact surface for atraumatically engaging the outer surface of the heart, and a mount having a first coupling for attachment to a chest retractor, a second coupling for attachment to the shaft, a first movable joint interconnected between the first and second couplings, and a second movable joint interconnected between the first joint and the second coupling. Preferably, each of the first and second joints is movable about at least two axes of rotation. For example, the first and second joints may comprise spherical joints or ball-in-socket joints. In one embodiment, the first joint comprises a first hemispherical member centered on a first axis and the second joint comprises a second hemispherical member centered on a second axis, the first and second axes being non-parallel, and preferably being generally perpendicular.

A further understanding of the nature and advantages of the invention may be realized by reference to the remaining portion of the specification and the drawings.

BRIEF DESCRIPTION OF THE DRAWINGS

FIGS. 14A–C are perspective, top and side views, respectively, of a heart retractor according to the invention.

DETAILED DESCRIPTION OF SPECIFIC EMBODIMENTS

Figure 1:
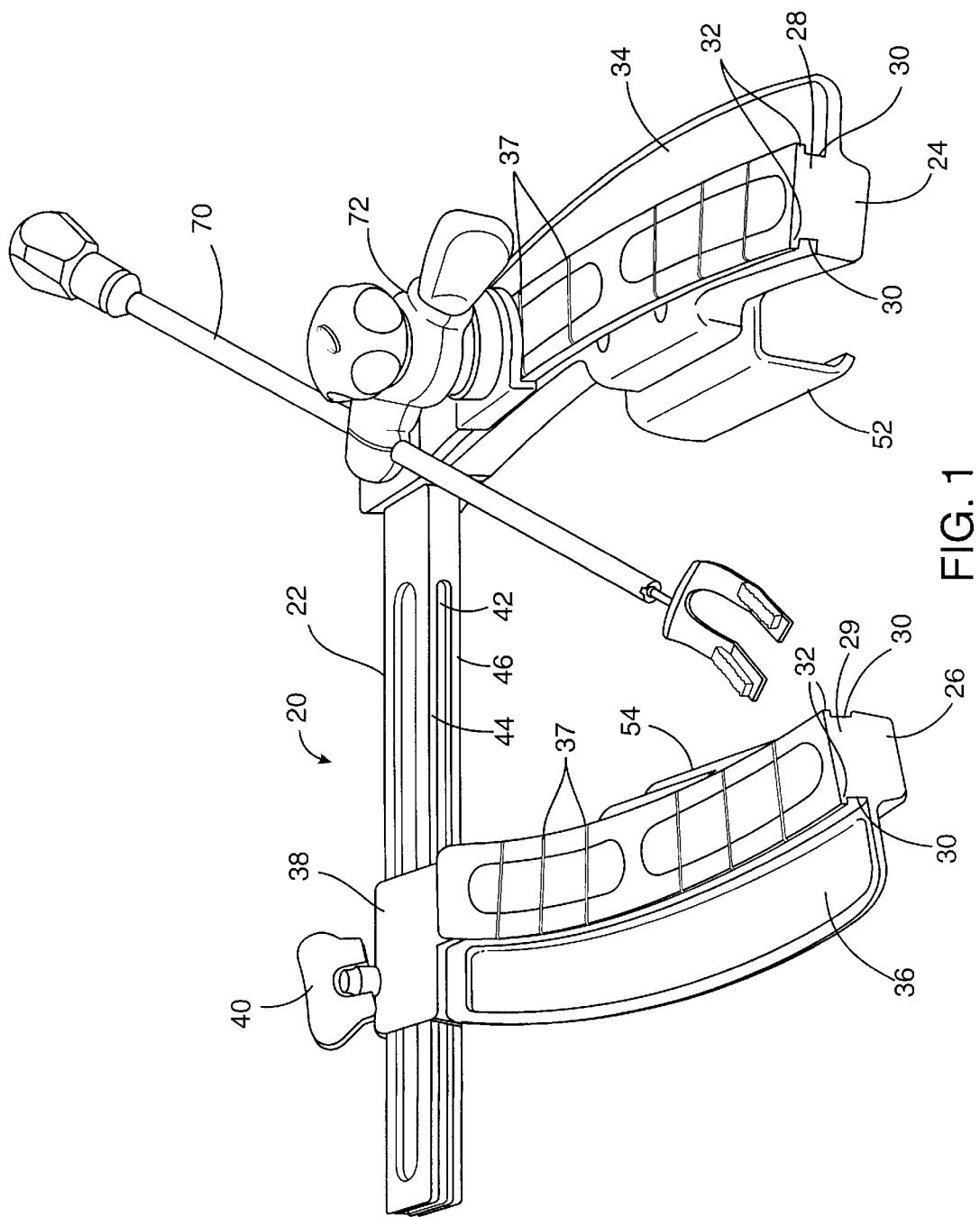
FIG. 1 is a perspective view of a retraction and stabilization system according to the invention.

A system for performing cardiac surgery according to the invention includes a retractor for retraction of a sternotomy or thorocotomy. The retractor has a pair of arms movable toward and away from each other and a pair of blades mounted to the arms which may be placed in a chest incision. The blades have contact surfaces facing away from each other which engage the opposing sides of the incision to allow retraction thereof. The arms preferably are mounted to a rack having a plurality of teeth, and at least one of the arms has a pinion gear which engages the teeth on the rack to facilitate movement of one arm relative to the other. In other embodiments, a cable-drive mechanism may be used rather than a rack and pinion, or the arms may be mounted directly to each other or to a third member by a rotational joint.

In a preferred embodiment, a rail is disposed on each arm of the retractor, and, if the two arms are connected to a rack, a rail is also disposed on the rack. Various accessory components may be coupled to the rails, including heart stabilizers, heart retractors and manipulators, $CO_2$ blowers, irrigators, suction devices, vascular clamps, lighting devices, catheters, and other devices. The rails are configured to allow slidable movement of such accessories components along the arms to a selected position.

The system of the invention will further include a stabilizer for stabilizing a surface of the heart. The stabilizer mounts to the retractor at any of various locations, preferably to one of the rails on the arms or rack of the retractor. The stabilizer includes a shaft and a foot, the foot being configured to atraumatically engage the surface of the heart to stabilize the surface while the heart is beating. The foot may have various configurations, including a bifurcated fork, partial or complete ring, or polygon, but will be suitable for stabilizing the heart adjacent to an anastomosis site to enable anastomosis of a graft vessel to a coronary artery. The foot may have a friction-enhancing surface to improve grip and minimize migration on the epicardium, which may be textured, knurled, roughened, or covered or coated with a friction-enhancing material. In a preferred embodiment, the foot is attached to the shaft by an articulating joint which may be locked and unlocked by means of an actuator coupled to the proximal end of the shaft. This allows the foot to be positioned at various orientations relative to the shaft according to the angle of approach and the location of the anastomosis site on the heart.

The stabilizer may optionally include one or more retainers which can be used for placement of sutures or silastics during an anastomosis or other procedure. The retainers are preferably located on the foot itself for proximity to the surgical site. The retainers are configured to retain the sutures or silastics in a state of tension, and have a clamping mechanism or are dimensioned for frictional engagement with the suture or silastic. In some embodiments, the retainers are removably attached to the stabilizer foot to allow the retainers to be removed when not needed or to be disposed of following the procedure.

The stabilizer is coupled to a mounting base which attaches to the rails of the retractor. The mounting base preferably includes at least two movable joints between the point of attachment to the rail and the point of attachment to the stabilizer, each joint having at least two axes of rotation. Preferably, the joints are spherical joints or ball-in-socket joints, thus maximizing the number of degrees of freedom available for positioning the stabilizer. The mounting base includes a coupling which attaches to the retractor rails, allows sliding movement thereon, and has a locking mechanism for locking the mounting base in a selected position on the rail.

The system may include a variety of other components and accessories useful in heart surgery. These include a heart retractor, which has a shaft, preferably malleable, and a paddle for engaging the heart. The paddle is preferably coated with a gauze or other atraumatic, friction-enhancing material to improve grip on the surface of the heart so as to facilitate rolling or lifting the heart. The system may also include a CO2 blower for emitting gas at the anastomosis site so as to keep it dry, clear of fluid and debris and thus visible to the surgeon. The blower preferably attaches to or is integrated into the stabilizer to facilitate positioning the blower outlet near the anastomosis site. A vascular clamp may also be provided which attaches to the rails of the retractor. The clamp may be used to temporarily clamp the end of a graft vessel such as the internal mammary artery and to hold it out of the surgical field until the surgeon is ready to use it. Various other devices may also be attached to the rails or other components of the system, including lighting, irrigation, suture retention, and retraction devices, as well as catheters and surgical instruments.

Referring now to the figures, FIG. 1 illustrates a first embodiment of a system for performing heart surgery according to the invention. The system includes a retractor 20 having a crossbeam 22, a stationary arm 24, and a movable arm 26. Stationary arm 24 and movable arm 26 have rails 28, 29 disposed along the top surface thereof, rails 28, 29 being defined by a pair of opposing side channels 30 forming a pair of lips 32 along the outer and inner upper edges of arms 24, 26. Stationary arm 24 and movable arm 26 further include wings 34, 36 extending outwardly from the lateral sides thereof. A plurality of channels 37 extend transversely across the top surfaces of stationary arm 24 and movable arm 26 and are dimensioned and configured for receiving a suture therein for retraction of the pericardium or other tissues, as described more fully below.

Movable arm 24 is attached to a carriage 38 slidably mounted to crossbeam 22. A key 40 is rotatably mounted to carriage 38 and is coupled to a pinion gear (described below) which engages a rack (described below) on crossbeam 22. In this way, movable arm 26 is movable toward and away from stationary arm 24 by rotating key 40. While stationary arm 24 is preferably mounted to crossbeam 22 so as to be unmovable, in some embodiments, both arms may be movably mounted to crossbeam 22 in the manner described above or in any other suitable manner. Crossbeam 22 further includes a pair of side channels 42 on its front and back edges each defining an upper lip 44 and a lower lip 46, thus forming a rail similar in construction to rails 28, 29 on stationary arm 24 and movable arm 26.

Figure 2:
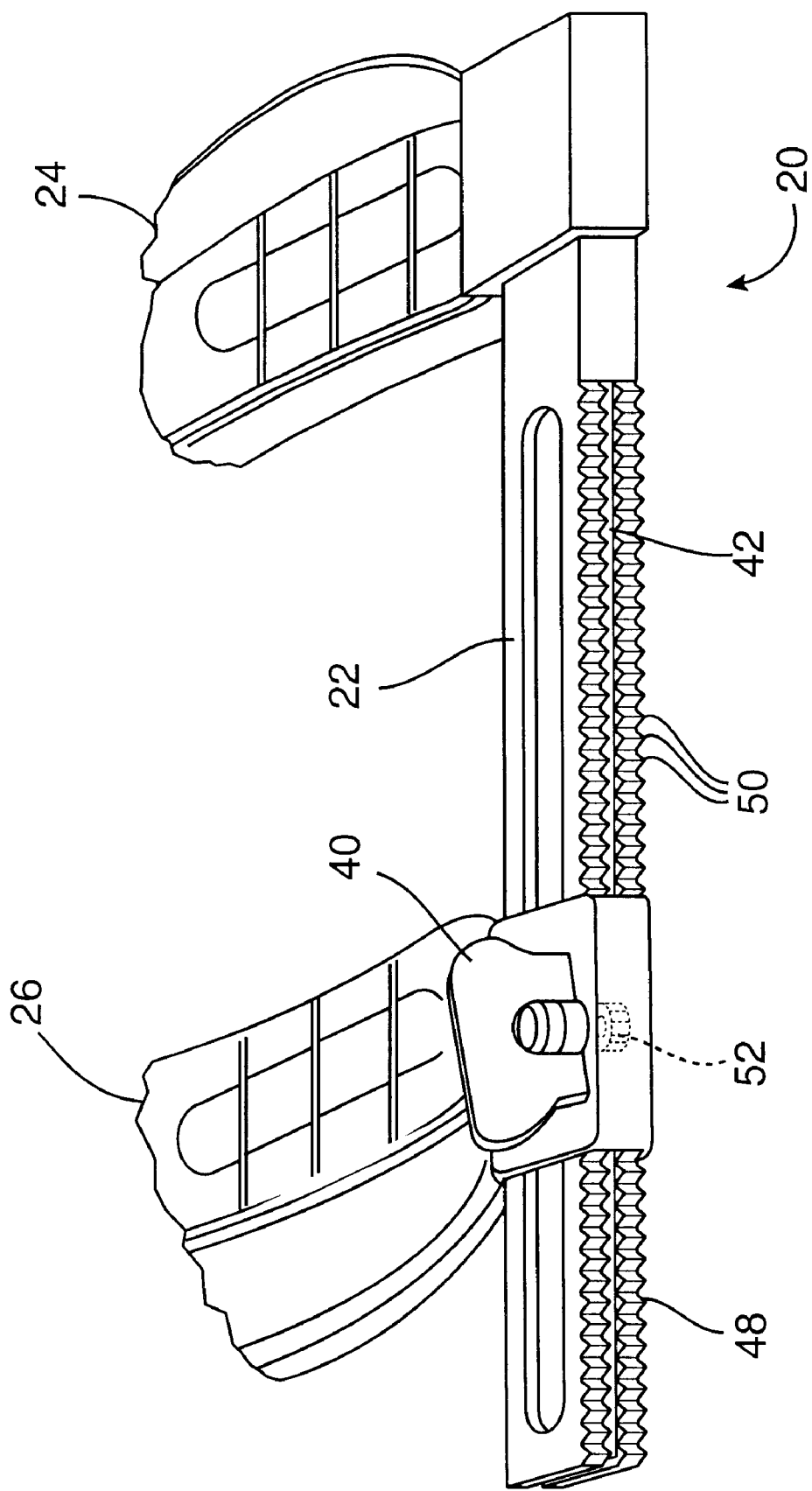
FIG. 2 is a partial perspective view of a retractor in the system of FIG. 1 showing a back side thereof.

Referring to FIG. 2, the back edge of crossbeam 22 forms a rack 48 having a plurality of linearly arranged gear teeth 50. Key 40 is coupled to a pinion gear 52 (shown in phantom) which engages rack 48, thus enabling movement of movable arm 26 by rotation of key 40. Side channel 42 extends longitudinally through rack 48, thus forming two parallel rows of gear teeth 50.

Figure 3:
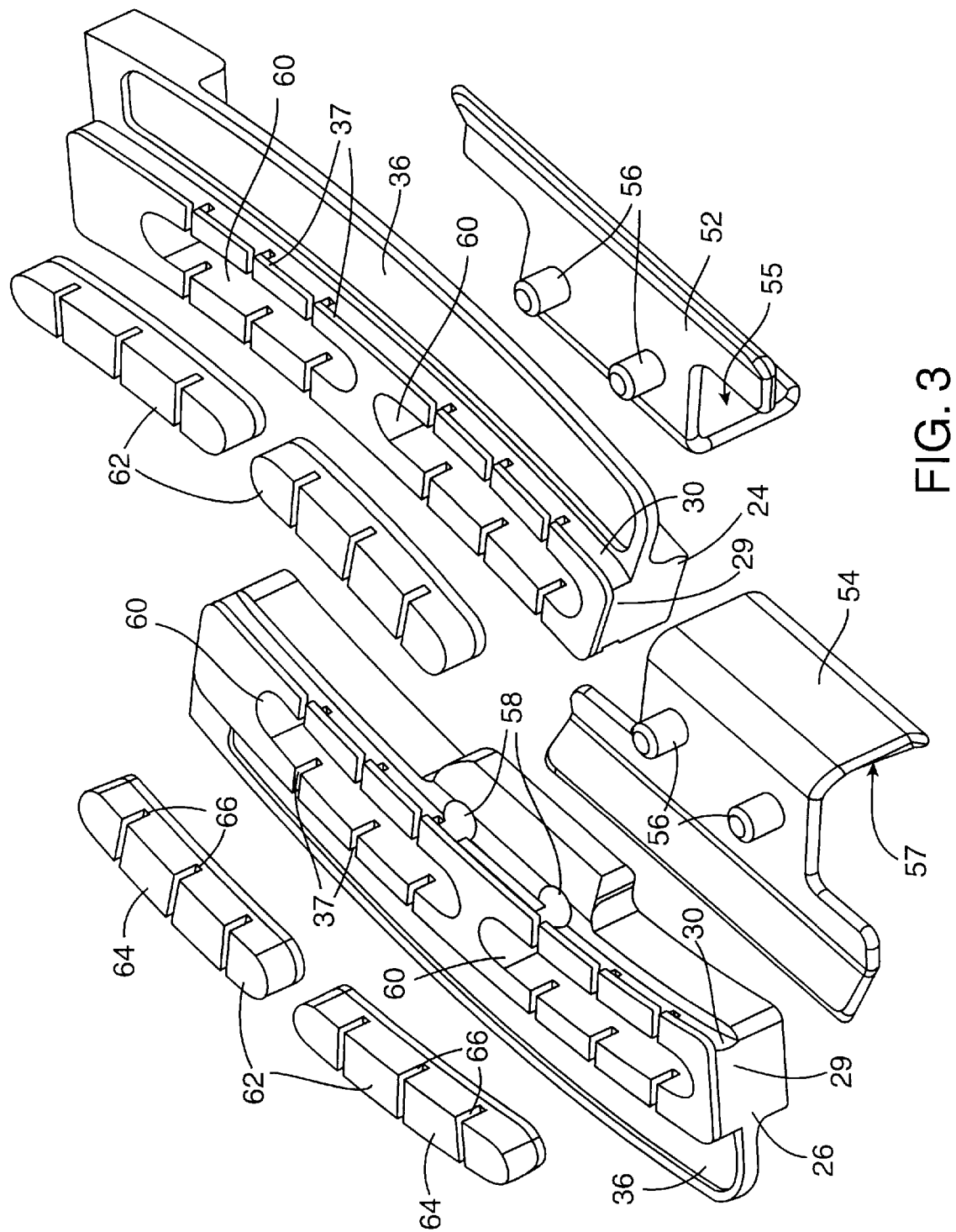
FIG. 3 is an assembly view of a stationary arm and a movable arm in the system of FIG. 1.

Referring again to FIG. 1, a first blade 52 is attached to stationary arm 24 and a second blade 54 is attached to movable arm 26. Preferably, first and second blades 52, 54 are removably coupled to arms 24, 26 to allow removal and interchange of various blades. As shown in FIG. 3, in which stationary blade 24 and movable blade 26 are shown removed from crossbeam 22 for clarity, first and second blades 52, 54 each have a pair of pins 56 which are slidably received in holes 58 in stationary arm 24 and movable arm 26. In this way, blades of various sizes and shapes may be easily interchanged according to the particular patient and procedure in which the device is being utilized. Blades 52, 54 have outwardly facing surfaces 55, 57 configured to atraumatically engage tissue or bone for retraction thereof.

In a preferred embodiment, crossbeam 22, stationary arm 24, movable arm 26, and first and second blades 52, 54 are all made of a biocompatible and sterilizable metal such as stainless steel, aluminum or titanium to allow resterilization and reuse after each procedure. However, it should be noted that any of these components may be made of an inexpensive material suitable for mass production, such as plastic, so that such components may be disposed of after a single use. In another exemplary embodiment, crossbeam 22 is metal so as to be reusable, while arms 24, 26 are plastic for single use and are removably attached to crossbeam 22 and carriage 38, respectively. Alternatively, crossbeam 22 and arms 24, 26 may be a reusable metal, while blades 52, 54 are a disposable plastic for single use.

Figure 4A:
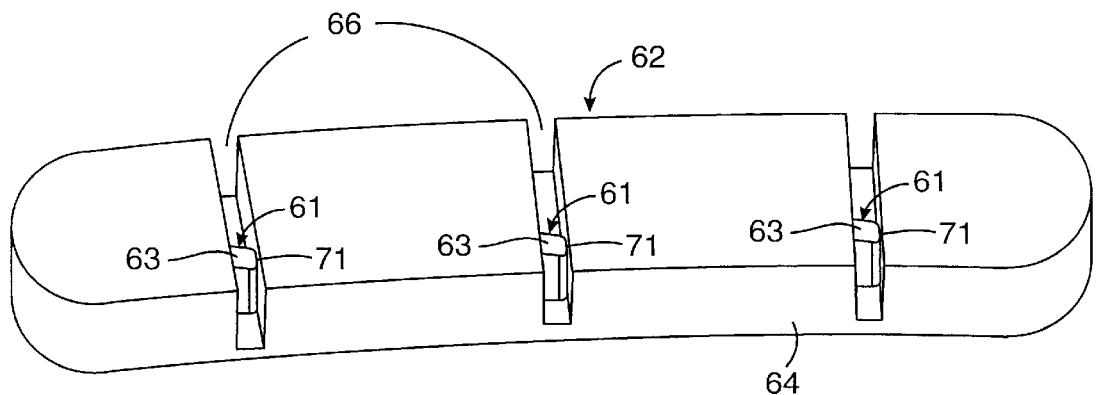
FIGS. 4A–B are top perspective and bottom perspective views, respectively, of a suture stay in the system of FIG. 1.
Figure 4B:
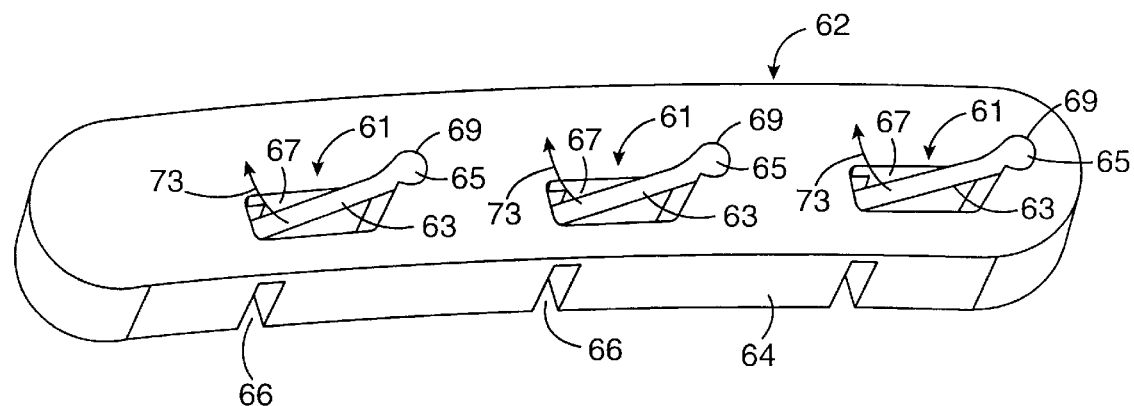
Figure 5:
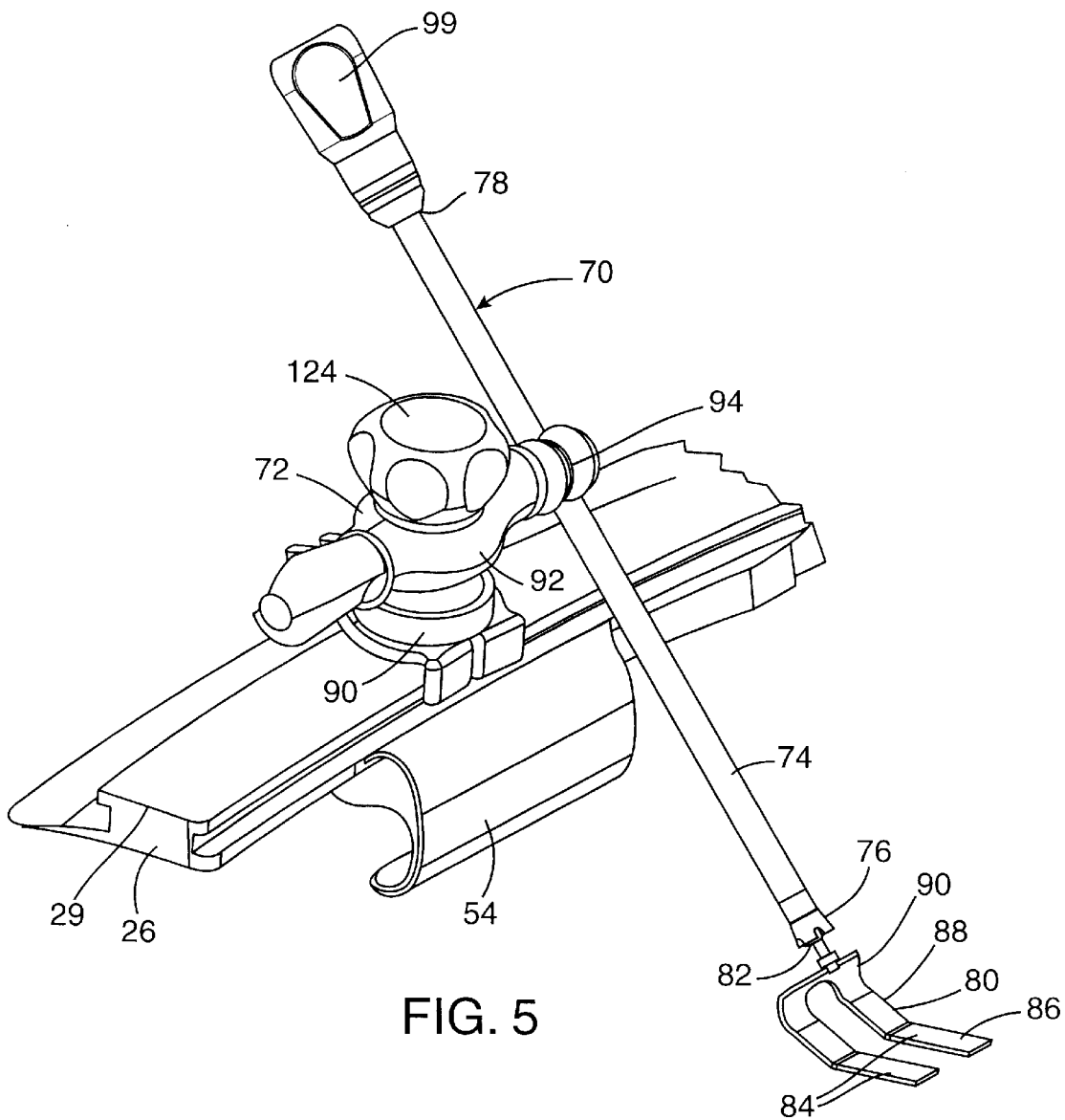
FIG. 5 is a perspective view of a stabilizer and mounting base mounted to an arm in the system of FIG. 1.
Figure 6:
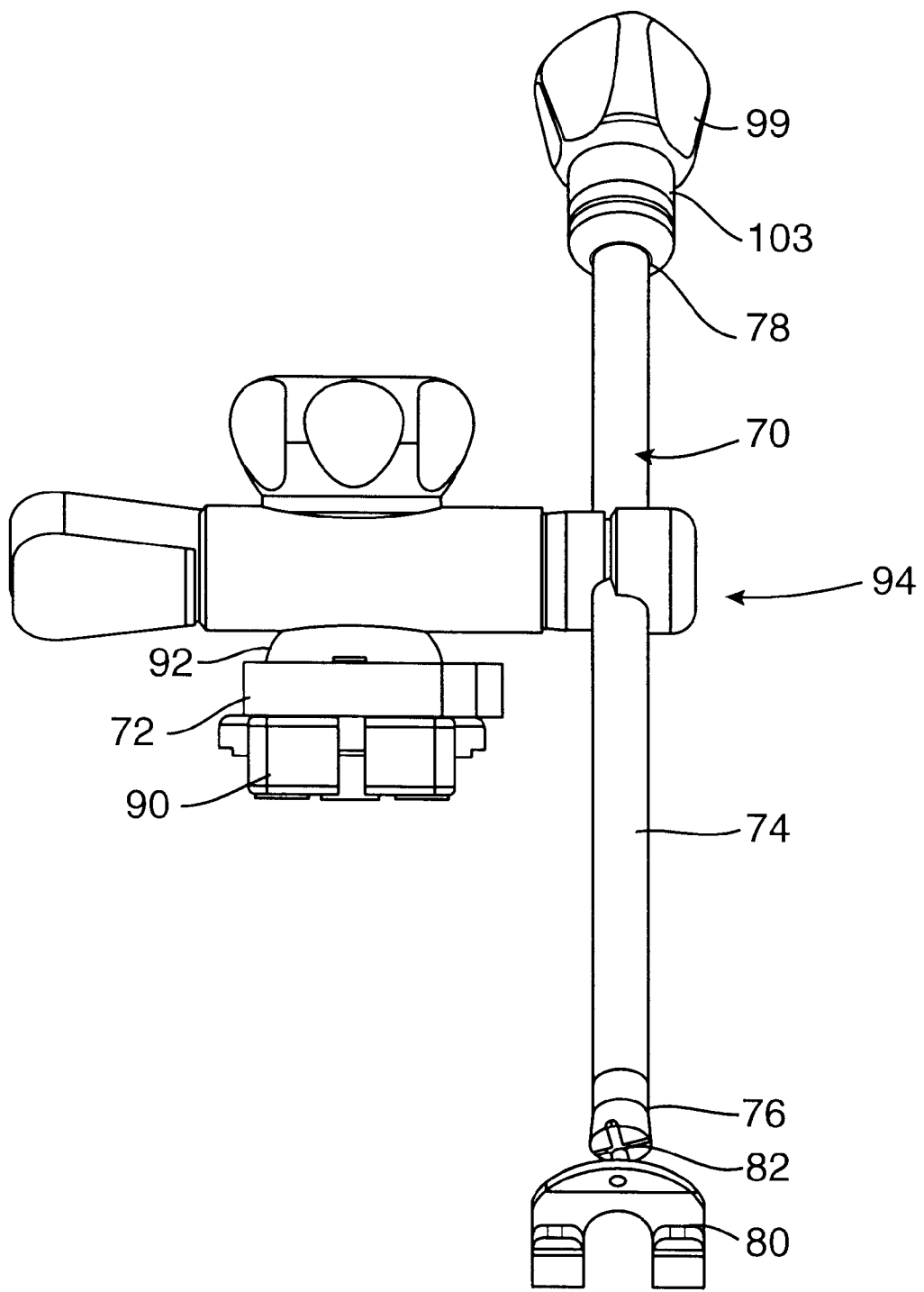
FIGS. 6–8 are front, side and top views, respectively, of the stabilizer and mounting base of FIG. 5.

Also shown in FIG. 3 are recesses 60 in the top surfaces of stationary arm 24 and movable arm 26 which are configured to receive suture stays 62. Suture stays 62 include a body 64 shaped for insertion into recess 60 and a plurality of slots 66 which align with channels 37 in arms 24, 26. As shown in FIGS. 4A–B, a clamp 61 is coupled to body 64 adjacent to each slot 66 and is configured to engage and retain a suture thread within slot 66. In an exemplary embodiment, each clamp 61 comprises a leaf 63 extending from a post 65. On the bottom side of body 62, an aperture 67 is disposed generally transverse to each slot 66 and has a bore 69 adjacent thereto. Posts 65 fit into bores 69, and leaves 63 are deflected so as to fit into apertures 67. In this way, leaves 63 are pre-loaded and biased into a clamping position in which their outer edges 71 are in engagement with the walls of slots 66. Outer edges 71 are deflectable in the direction of arrows 73 to allow a suture to be drawn into slots 66, but are biased back into engagement with the suture to clamp it in place.

Returning to FIG. 1, the system of the invention further includes a stabilizer 70 for stabilizing the surface of the heart or other organ during a surgical procedure. Stabilizer 70 may be mounted either to rails 28, 29 or to crossbeam 22 by means of a mounting base 72. As shown more clearly in FIGS. 5–8, stabilizer 70 includes a shaft 74 having a distal end 76 and a proximal end 78. A foot 80 is pivotably mounted to distal end 76 by means of a ball joint 82. Foot 80 is configured to engage the surface of the heart on opposing sides of an anastomosis site, preferably having a pair of arms 84 generally parallel to each other and spaced apart by a distance in the range of about 1–5 cm. Arms 84 have a generally flat portion 86 for engaging the heart, an angled portion 88 sloping upwardly from flat portion 86, and a proximal portion 90 which connects arms 84 and may have a curved, angled, or other suitable shape for attachment to a stem 92 coupled to ball joint 82. The bottom surfaces of arms 84 are adapted for atraumatic engagement with the epicardium, usually being smooth and flat. In a preferred embodiment, a friction-enhancing element is disposed on the bottom surfaces of flat portions 86. For example, the bottom surfaces may be textured with grooves, ribs, knurling, projections or other features, or they may be coated or covered with a friction-enhancing material such as foam, Dacron gauze, no-slip material, or a roughened or textured metal or plastic plate. Such material will enhance friction with the epicardium sufficiently to prevent slippage and migration of the foot, but not to such an extent as to injure the epicardial tissue.

Figure 7:
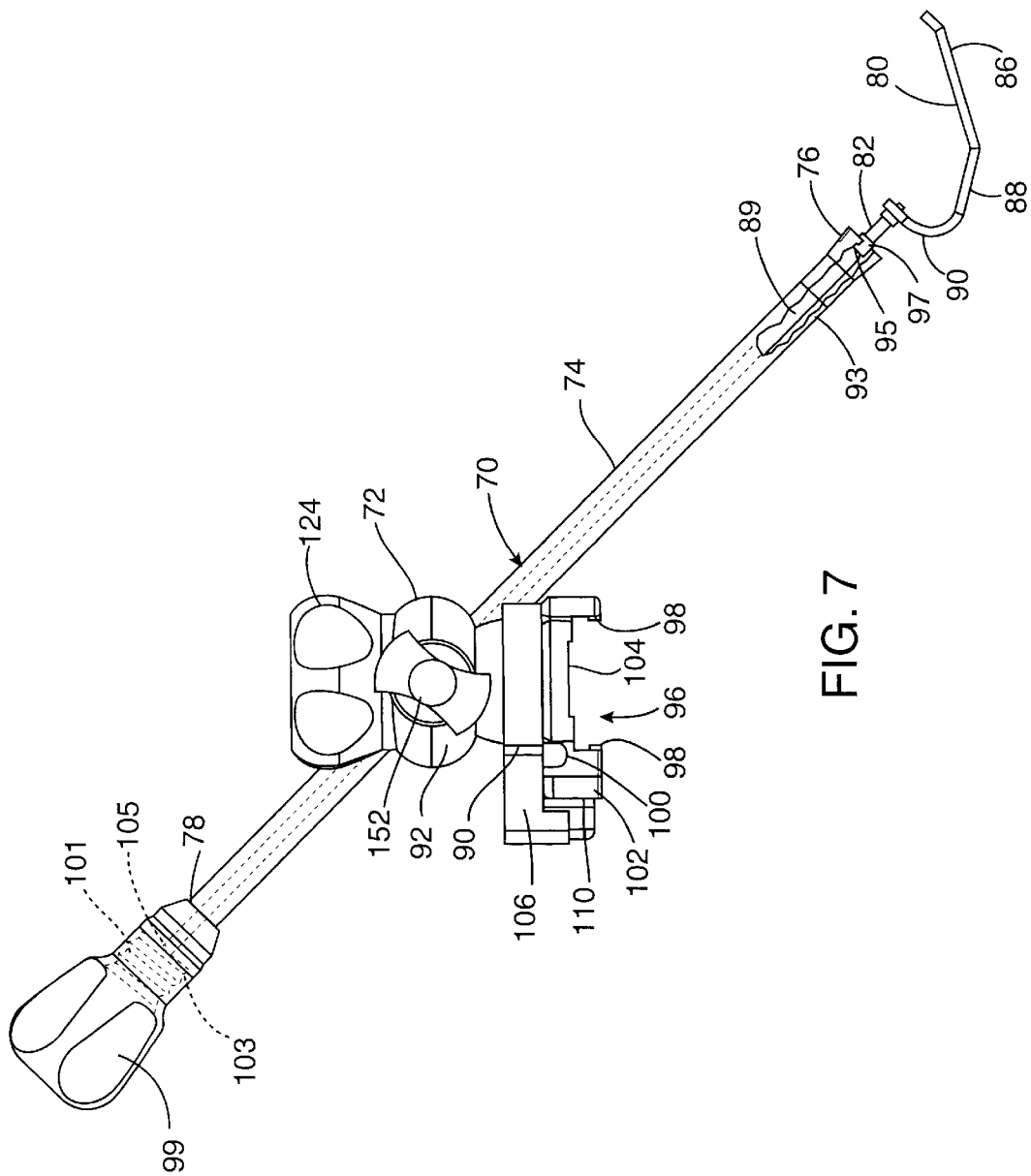
Figure 8:
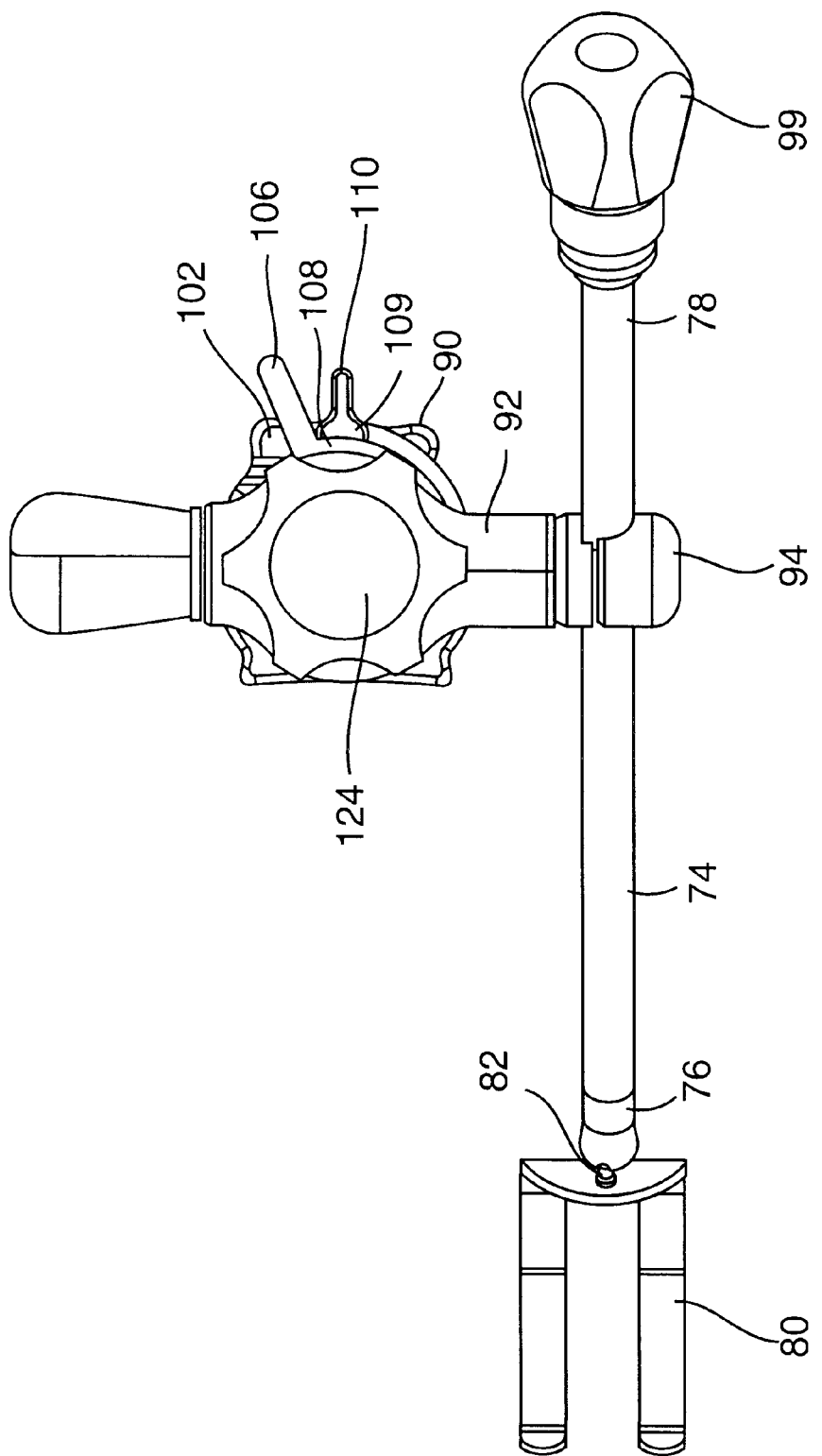

For purposes of locking foot 80 in a selected position relative to shaft 74, a rod 89 is slidably disposed within a channel 93 in shaft 74, as shown in FIG. 7. Rod 89 has a distal end 95 which engages ball 97 of ball joint 82. An actuator on the proximal end of shaft 74 has a rotatable knob 99 having a threaded body 101 which is received in a threaded socket 103 attached to shaft 74. A distal end of threaded body 101 is attached to proximal end 105 of rod 89. In this way, rotation of knob 99 drives rod 89 distally into tight, locking engagement with ball 97, thus locking foot 80 in position.

It should be understood that stabilizer 70 and foot 80 may have various other configurations and features. For example, foot 80 may have an annular ring shape or angular polygonal shape, or have simply a single heart-engaging arm. Stabilizer 70 may further have a suction lumen and suction holes or cups on the bottom surface of foot 80 in order to apply suction to the epicardium for enhanced stability and immobility. Other features and configurations may also be provided, such as those described in U.S. Pat. No. 5,807,243, assigned to the assignee of the present application and hereby incorporated herein by reference.

Mounting base 72 includes a carriage 90 adapted for slidable engagement with rails 28, 29, a turret 92 rotatably mounted to carriage 90, and a clamp 94 rotatably mounted to turret 92. Carriage 90 has a channel 96, as shown in FIG. 7, configured to slide onto rails 28, 29 or crossbeam 22. Channel 96 has a pair of inwardly projecting lips 98 configured to be positioned within side channels 30 in arms 24, 26 or side channels 42 in crossbeam 22. For the purpose of clamping carriage 90 in a selected position along rails 28, 29 or crossbeam 22, carriage 90 has a living hinge 100 which allows an outer portion 102 of carriage 90 to rotate toward and away from an inner portion 104. A lever 106 is rotatably mounted to carriage 90 and has a sloped cam 108 which engages a camming surface 109 on outer portion 102 so as to urge it toward inner portion 104 as lever 106 is actuated in the clockwise direction (see FIG. 8). This locks carriage 90 in place along rails 28, 29 or crossbeam 22. Rotating lever 104 in the opposite direction allows outer portion 102 to rotate away from inner portion 104, thus allowing carriage 90 to be slid along or removed from rails 28, 29 or crossbeam 22. A stationary finger grip 110 is mounted to outer portion 102 of carriage 90 to enhance leverage during actuation of lever 104.

Figure 9:
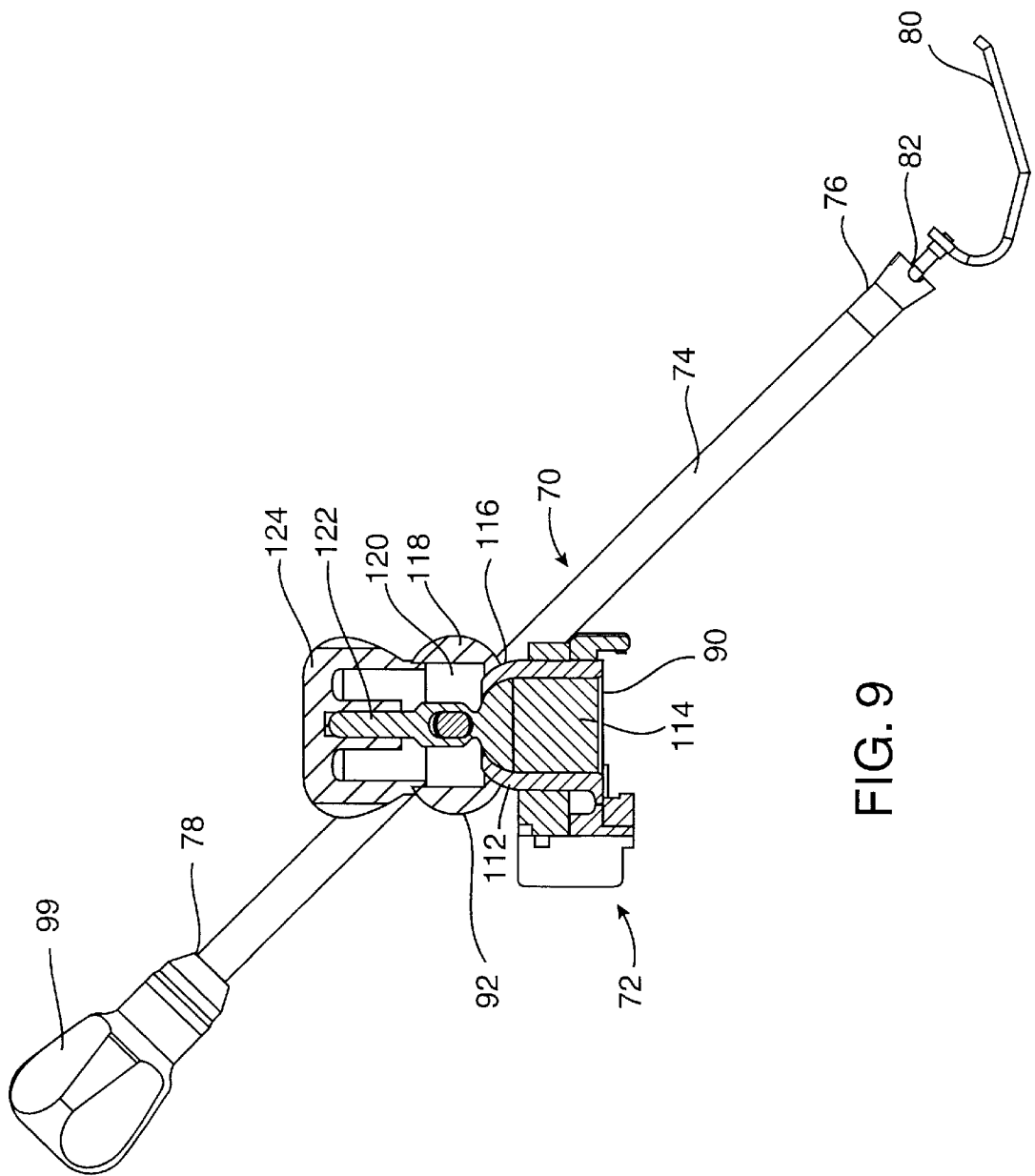
FIG. 9 is a side cross-section through the mounting base of FIG. 5.

Referring to FIG. 9, turret 92 preferably provides rotation about at least two axes. In an exemplary embodiment, turret 92 comprises a spherical joint 112 having a base 114 attached to carriage 90 with a hemispherical top surface 116, and a socket 118 having a cavity 120, whereby socket 118 is rotatable about multiple axes relative to base 114. In order to secure socket 118 in a given position relative to base 114, a threaded post 122 is secured to base 114, extends upwardly through socket 118 and is coupled to a threaded cap 124 having a lower end in engagement with socket 118. In this way, socket 118 may be locked in a selected position by tightening cap 124 on post 122, thus pressing socket 118 into engagement with base 114.

Figure 10:
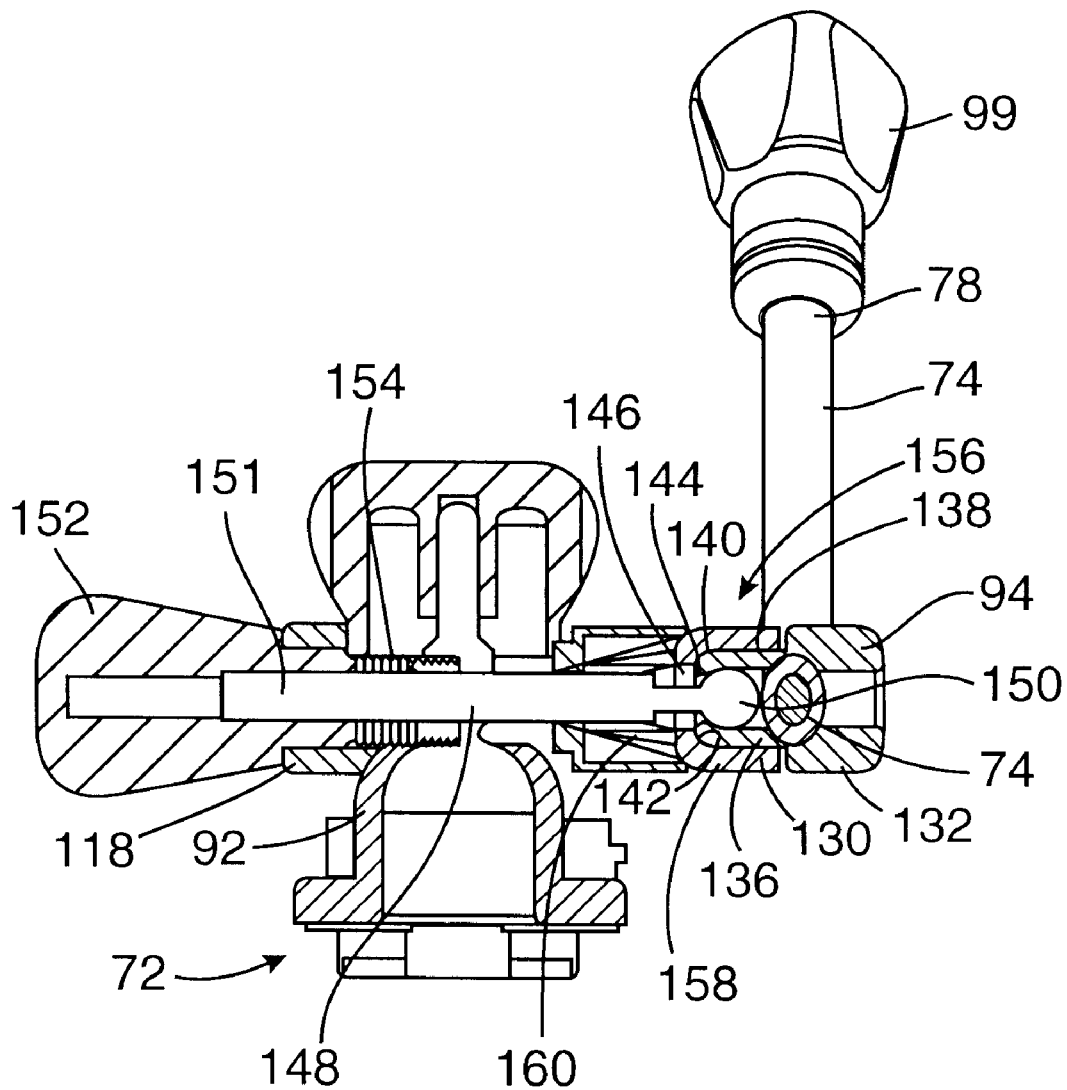
FIG. 10 is a front cross-section through the mounting base of FIG. 5.

Referring to FIG. 10, clamp 94 is configured to hold shaft 74 of stabilizer 70, or any of various other surgical instruments and devices utilized with the invention. Like turret 92, clamp 94 preferably provides rotation about at least two axes. In an exemplary embodiment, clamp 94 has an inner member 130 and an outer member 132. Outer member 132 has a bore 134 in which shaft 74 is slidably positioned. A cylindrical extension 136 on outer member 132 is slidably received within a cavity 138 in inner member 130. Cylindrical extension 136 has a tapered inner end 140 which engages a tapered surface 142 in cavity 138. Tapered inner end 140 has an opening 144 and inner member 130 has an opening 146 through which a rod 148 extends. Rod 148 has a ball 150 on its outer end which resides within cylindrical extension 136 and is retained therein by tapered inner end 140, opening 144 being smaller than ball 150. Rod 148 extends through socket 118 of turret 92 and has a threaded end 151 opposite ball 150. A threaded knob 152 engages threaded end 151, allowing outer member 132 to be drawn toward inner member 130 by rotating knob 152, thus clamping shaft 74 in bore 134. A spring 154 is disposed around threaded end 151 and engages knob 152 urging it outwardly. This provides a small amount of clamping force on shaft 74 even when knob 151 is loosened, preventing the inadvertant slippage of stabilizer 70 into the surgical site.

Clamp 94 preferably also includes a spherical joint 156 to provide additional degrees of freedom for positioning stabilizer 70. Inner member 130 has a hemispherical outer end 158 which is received in a clamp socket 160 attached to socket 118 of turret 92. Clamp socket 160 may be a conical, spherical, or otherwise tapered concavity allowing rotation of inner and outer members 130, 132 about multiple axes relative to turret 92. Opening 146 in inner member 130 has tapered edges and is sufficiently large to allow a wide range of rotational movement of inner member 130 about rod 148. Spherical joint 156 is locked in a selected position in the same way as clamp 94, by tightening knob 152, which pulls on rod 148 thus urging inner member 130 into tight engagement with clamp socket 160.

Figure 11:
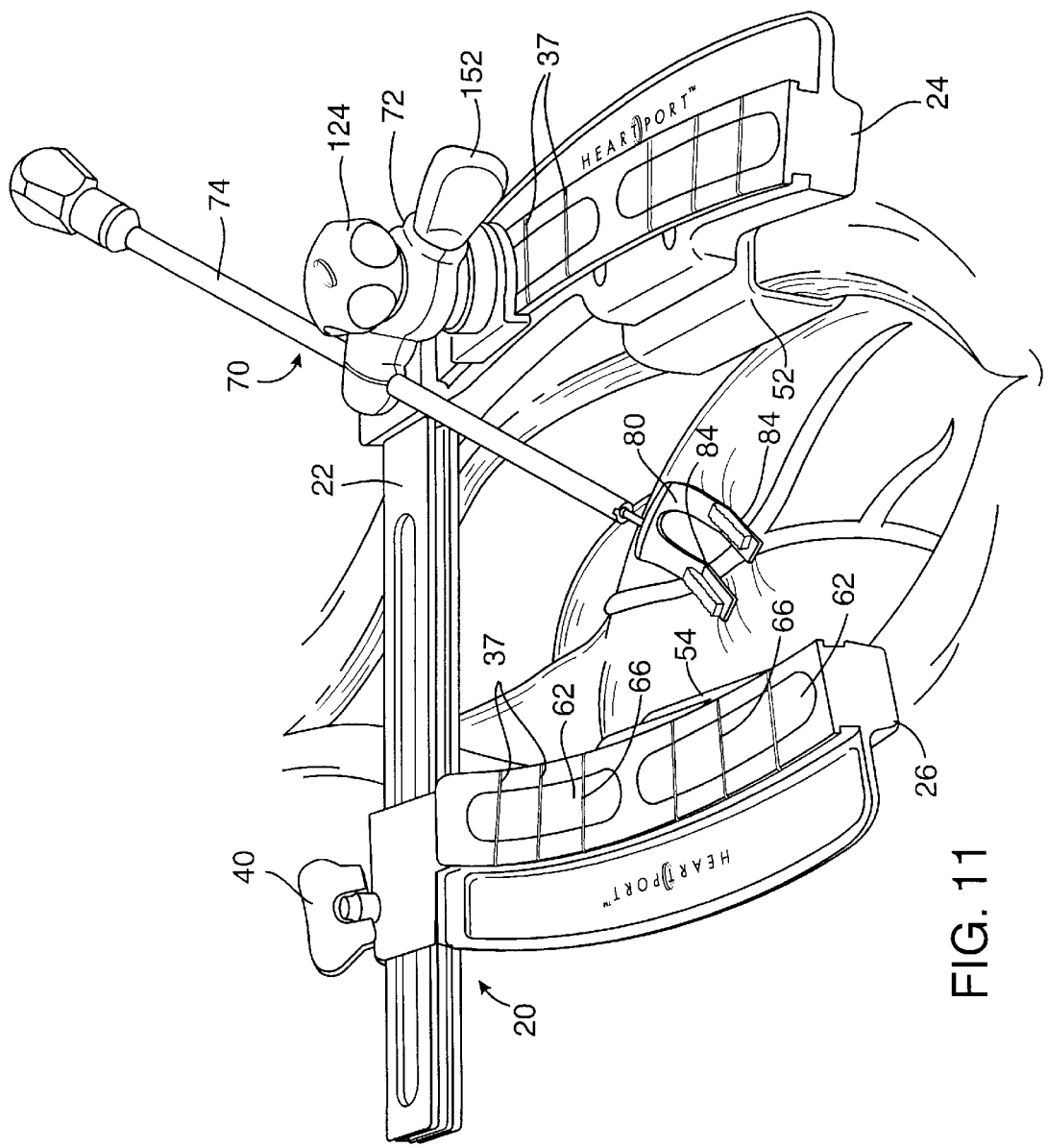
FIG. 11 is a perspective view of the system of FIG. 1 in position in an incision in a patient's chest.

In use, retractor 20 of the invention is placed in sternotomy incision as shown in FIG. 11. First and second blades 52, 54 of appropriate size and shape are attached to stationary arm 24 and movable arm 26. Movable arm 26 is positioned close to stationary arm 24 so that blades 52, 54 can be inserted into the incision. Key 40 is then turned to move movable arm 26 away from stationary arm 24, whereby by first and second blades 52, 54 retract the opposing tissue edges and widen the incision to expose the chest cavity. An incision is made in the pericardium (not shown in FIG. 11) and sutures are placed in the pericardial flaps. The sutures are drawn out of the chest and placed through channels 37 into slots 66 in suture stays 62, and tensioned until the pericardial flaps are drawn out of the way to expose the surgical site on the heart. The pericardial sutures may then be clamped in position in suture stays 62.

When it is time to perform the coronary anastomosis, mounting base 72 for stabilizer 70 is positioned along one of rails 28, 29 or on crossbeam 22 at the desired position, and lever 104 is actuated to lock mounting base 72 in position. Stabilizer 70 is then positioned so that foot 80 engages the epicardium near the anastomosis site. Usually, arms 84 are positioned on opposing sides of the target coronary artery aligned with the anastomosis site. Alternatively, one of arms 84 may be positioned so as to engage the coronary artery itself upstream of the anastomosis site to occlude the coronary artery to provide hemostasis during the anastomosis. Once positioned, stabilizer 70 is locked in position by tightening cap 124 and knob 152. Stabilizer 70 maintains relative stillness in the heart wall in the area of the anastomosis, while the heart continues to beat and the remainder of the heart wall contracts.

Figure 12A:
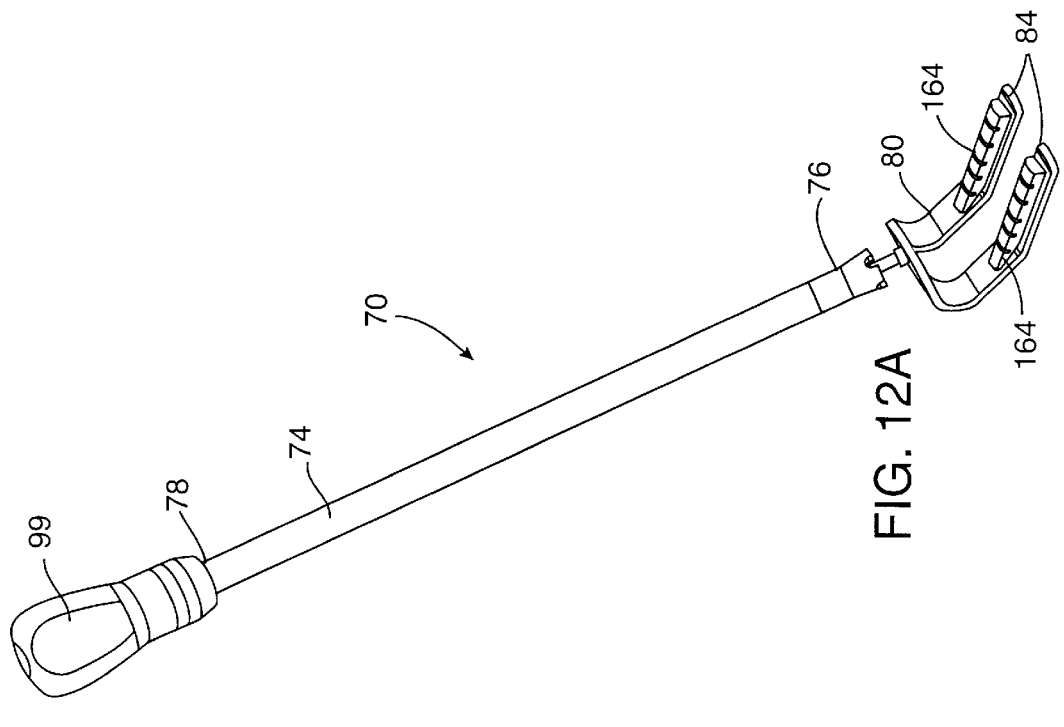
FIG. 12A is a prespective views of a further embodiment of a stabilizer according to the invention.
Figure 12B:
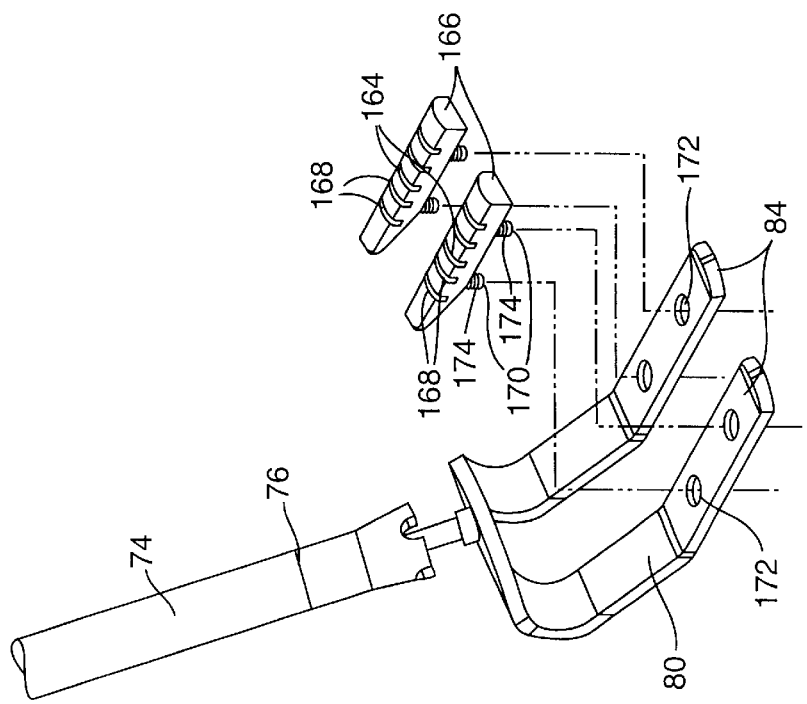
FIG. 12B is a perspective assembly view of a distal portion of the stabilizer of FIG. 12A.

FIGS. 12A–12B illustrate an additional embodiment of stabilizer 70 of the invention. In this embodiment, stabilizer 70 includes a pair of suture retainers 164 which may be mounted to foot 80. Preferably, retainers 164 are removable from foot 80 so that stabilizer 70 may be used with or without retainers 164 in place. Retainers 164 have a body 166 and a plurality of channels 168 configured to receive a suture or silastic used in the particular surgical procedure being performed. Channels 168 are dimensioned to frictionally engage the suture or silastic material with sufficient force to retain the material under tension, preferably having a width of about 0.010–0.030 in. and a depth of about 0.10–0.20 in, depending upon the type and size of suture or silastics utilized. In this way, sutures or silastics may be placed under the target coronary artery so as to form a sling on one or both sides of the anastomosis site, and the sutures or silastics may be tensioned to better expose the coronary artery relative to the surrounding myocardium, as well as to occlude the coronary artery for hemostasis. The sutures or silasatics may then be placed in channels 168 and are retained therein under tension during the procedure. In a preferred embodiment, retainers 164 have two pins 170 which extend from the bottom surfaces thereof and are received in holes 172 in foot 80. Pins 170 have flanges 174 which snap into holes 172 and retain pins 170 therein. Retainers 164 and pins 170 may be metal, rubber or plastic.

Figure 13:
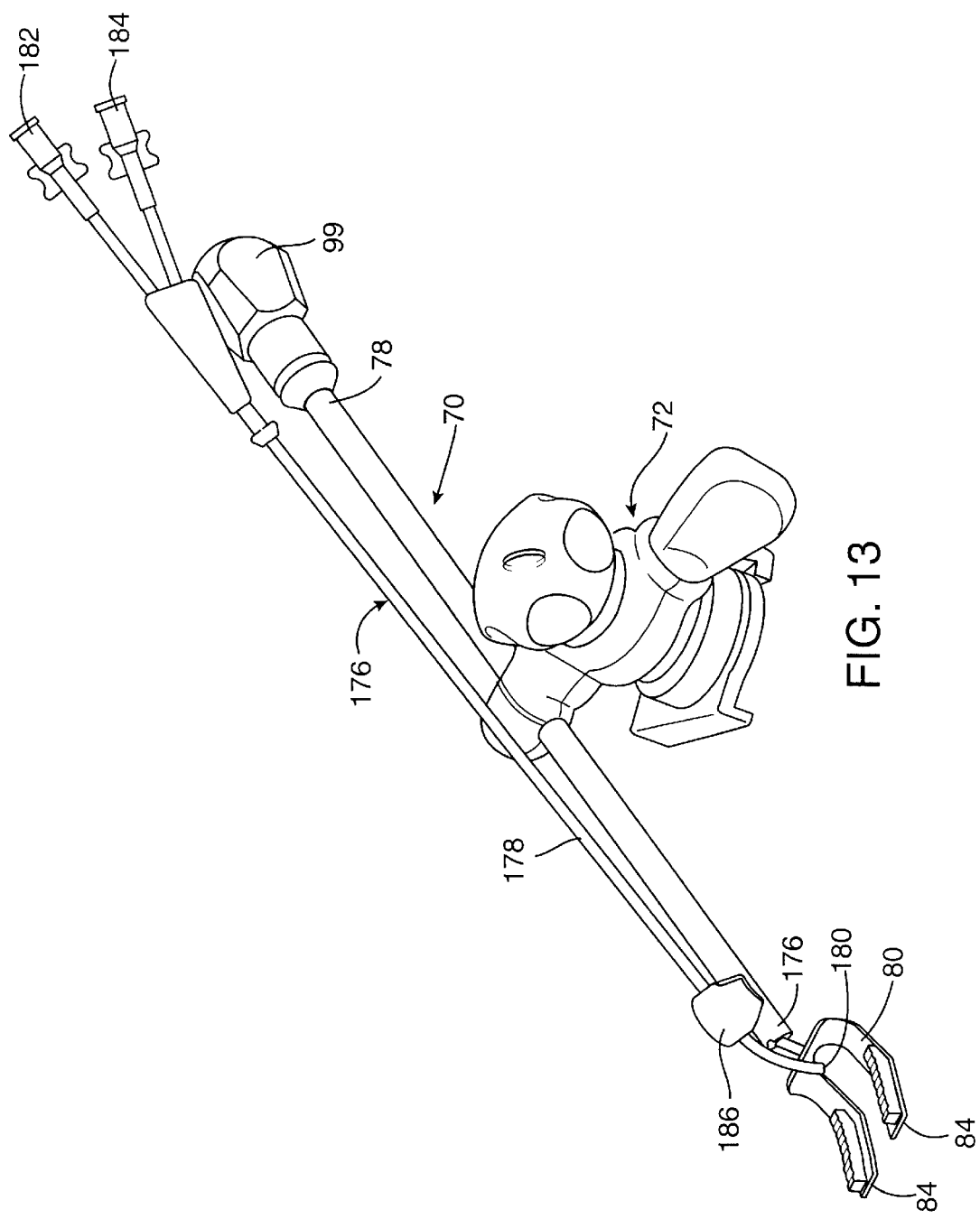
FIG. 13 is a perspective view of a stabilizer and blower according to the invention.

FIG. 13 illustrates an additional embodiment of stabilizer 70 of the invention. In this embodiment, a blower 176 is coupled to stabilizer 70 to allow for the delivery of a gas such as $CO_2$ to the surgical site. This helps to keep the site free of fluids and debris, as well as helps to inhibit the introduction of oxygen into the coronary arteriotomy. Blower 176 includes a shaft 178 having at least one inner lumen extending therethrough. Preferably, a second inner lumen is also provided. The inner lumens communicate with at least one opening at the distal end 180 of shaft 178, and with inlet ports 182,184 at the proximal end of shaft 178. Inlet port 182 may be connected to a supply of gas such as $CO_2$, while inlet port 184 may be connected to a source of saline for irrigating or misting the surgical site, or to a source of suction for aspirating fluid and debris. Both inlet ports 182, 184 may be in communication with a single inner lumen in shaft 178, or each inlet port may be in communication with a separate inner lumen in the shaft. At least one clip 186 is attached to shaft 178 and is configured to be removably coupled to shaft 78 of stabilizer 70. Preferably, blower 176 is positionable such that its distal end 180 is disposed between arms 84 of foot 80 and close to the proximal end of the foot so as to deliver or suction fluids from the site without interfering with the anastomosis.

Figure 14A:
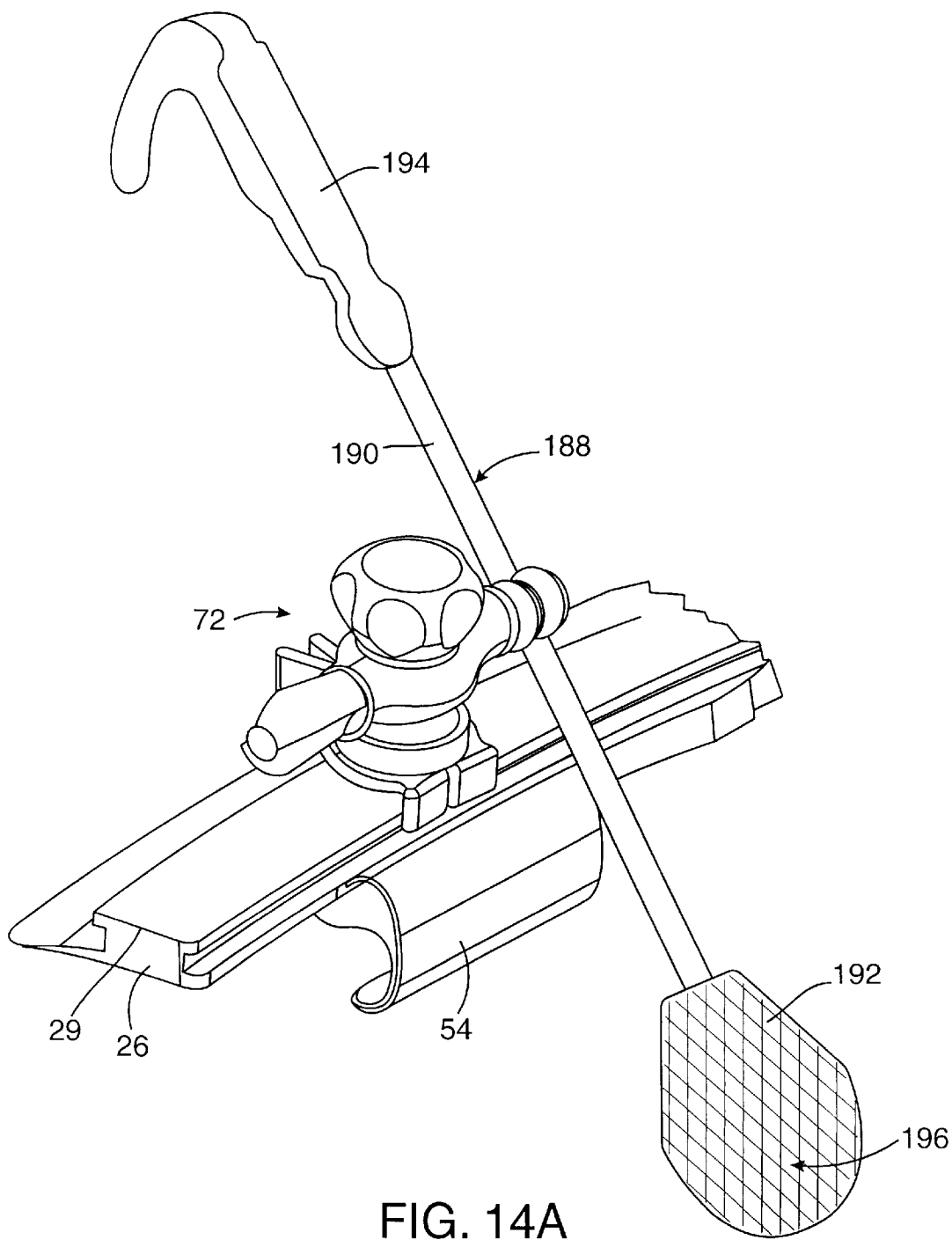

FIGS. 14A–14C illustrate a heart retractor which may be utilized with the system of the invention. Heart retractor 188 has a shaft 190 with a paddle 192 at its distal end and a handle 194 at its proximal end. Paddle 192 is covered with a soft, friction-enhancing and preferably absorbent material 196 such as adhesive-backed Dacron gauze. Paddle 192 is dimensioned to enable engagement with the outer wall of the heart and rolling, lifting or pushing the heart into a desired location during a surgical procedure, preferably having a width of about 1–3 inches and a length of about 2–4 inches across its face. Handle 194 is configured to be gripped by a surgeon's hand and is lightweight and compact, preferably being made of a lightweight plastic. Heart retractor 188 is preferably clamped onto rails 28, 29 or crossbeam 22 by means of mounting base 72 utilized with stabilizer 70, as described above. In this way, heart retractor 188 may be used to manipulate the heart into a desired position, and the heart retractor may be locked in place on retractor 20 to maintain the heart in position while an anastomosis or other procedure is performed. This facilitates the performance of anastomoses on the sides and back of the heart to enable multi-vessel coronary bypass procedures.

Figure 15A:
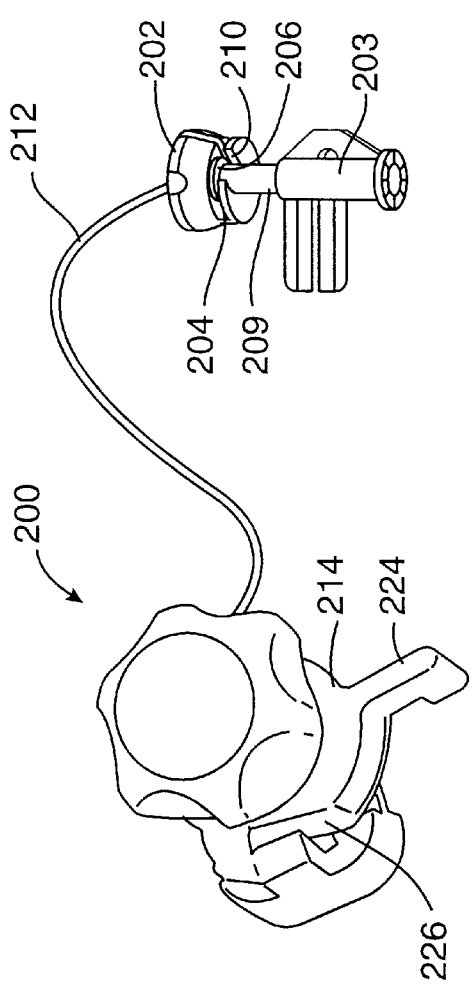
FIGS. 15A–15B are perspective and side views, respectively, of a vascular clamp holder according to the invention.
Figure 15B:
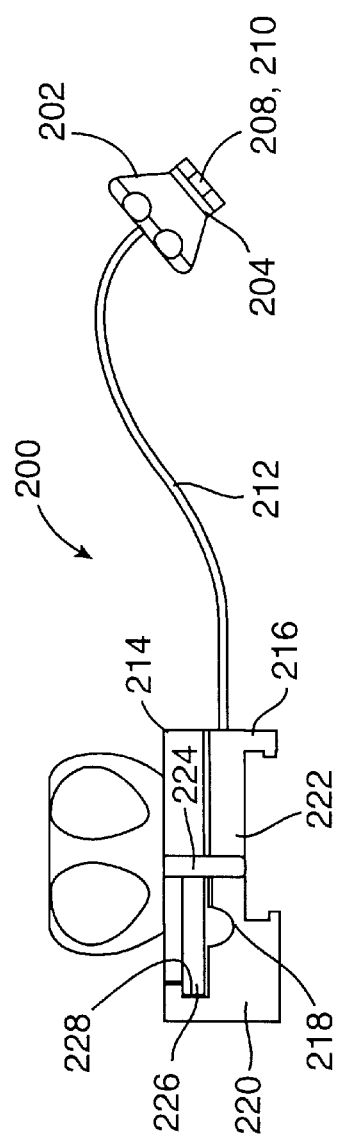

FIGS. 15A–B illustrate a vascular clamp holder that may be utilized with the system of the invention. Vascular clamp holder 200 includes a clip 202 configured to removably attach to a commercially-available vascular clamp 203 such as a Fogarty Clamp, as shown. Clip 202 has a slot 204 configured to receive a button 206 on the vascular clamp, and an axial channel 208 through which a shaft 209 of the vascular clamp may extend. Axial channel 208 has a side opening 210 through which shaft 209 may be placed in the channel, the side opening preferably having a width slightly smaller than shaft 209 so that the shaft is maintained in channel 208 once inserted therein. A malleable rod 212 extends from clip 202 to mount 214 and may be shaped in order to place clip 202 in a desired position. Mount 214 is configured to be attached to rails 28, 29 or crossbeam 22 on retractor 20, and may be constructed in a manner similar to that described above for mounting base 72. However, mount 214 need not have the same degree of positionability as mounting base 72, allowing both spherical joints to eliminated. Thus, mount 214 has a carriage 216 like carriage 90 described above, and is adapted for slidable engagement with rails 28, 29 or crossbeam 22. Carriage 216 has a living hinge 218 about which an outer portion 220 rotates relative to inner portion 222. A rotatable lever 224 has a cam 226 which engages a camming surface 228 on outer portion 220 to urge it against rails 28, 29 or crossbeam 22, thus locking mount 214 in place.

While the above is a complete description of the preferred embodiments of the invention, it will be appreciated that various equivalents, modifications, additions and substitutions may be made without departing from the scope thereof. Therefore, the above should not be taken as limiting the scope of the invention, which is defined by the following claims.

What is claimed is:

1. Apparatus for performing surgery on a heart of a patient, comprising:
   a first arm, a second arm and an actuator, the actuator moving the first arm relative to the second arm, at least one of the first and second arms having a receptacle thereon;
   a first blade on the first arm and a second blade on the second arm, the first and second blades having first and second surfaces facing away from each other, the first and second surfaces being adapted to atraumatically engage tissue or bone for the retraction thereof;
   a stabilizer adapted to be coupled to one of the first and second arms and having a foot, the foot being configured to atraumatically engage the surface of the heart; and
   a suture stay removably mounted to the receptacle.

2. The apparatus of claim 1 wherein the first and second arms are metal.

3. The apparatus of claim 2 wherein the suture stay is plastic.

4. The apparatus of claim 1 wherein suture stay is contained in a sterile package separate from the first and second arms and the first and second blades.

* * * * *